US005464016A

United States Patent [19]

Nicholas et al.

[11] Patent Number: 5,464,016

[45] Date of Patent: Nov. 7, 1995

[54] MEDICAL ACOUSTIC IMAGING CATHETER AND GUIDEWIRE

[75] Inventors: Peter M. Nicholas, South Dartmouth; Robert J. Crowley, Wayland, both of Mass.

[73] Assignee: Boston Scientific Corporation, Watertown, Mass.

[21] Appl. No.: 355,435

[22] Filed: Dec. 13, 1994

Related U.S. Application Data

[63] Continuation of Ser. No. 67,348, May 25, 1993, abandoned, which is a continuation-in-part of Ser. No. 66,990, May 24, 1993, abandoned.

[51] Int. Cl.$^6$ .......... A61B 8/12

[52] U.S. Cl. .......... 128/662.06; 128/772

[58] Field of Search .......... 128/662.06, 660.03, 128/772

[56] References Cited

U.S. PATENT DOCUMENTS

| | | | |
|---|---|---|---|
| 4,899,757 | 2/1990 | Pope, Jr. et al. | 128/662.06 |
| 4,911,170 | 3/1990 | Thomas, III et al. | 128/662.06 |
| 4,936,307 | 6/1990 | Saito et al. | 128/662.06 |
| 4,951,677 | 8/1990 | Crowley et al. | 128/662.06 |
| 5,000,185 | 3/1991 | Yock | 128/662.06 |
| 5,002,059 | 3/1991 | Crowley et al. | 128/662.06 |
| 5,010,886 | 4/1991 | Passafaro et al. | 128/660.03 |
| 5,049,130 | 9/1991 | Powell | 604/96 |
| 5,090,414 | 2/1992 | Takano | 128/662.05 |
| 5,095,911 | 3/1993 | Pomeranz | 128/662.06 |
| 5,108,411 | 4/1992 | McKenzie | 606/159 |
| 5,115,814 | 5/1992 | Griffith et al. | 128/662.06 |
| 5,166,073 | 11/1992 | Lefkowitz et al. | 436/57 |
| 5,176,141 | 1/1993 | Bom et al. | 128/662.06 |
| 5,201,316 | 4/1993 | Pomeranz et al. | 128/662.06 |
| 5,240,003 | 8/1993 | Lancee et al. | 128/662.06 |
| 5,305,755 | 4/1994 | Nakao | 128/660.08 |
| 5,325,860 | 7/1994 | Seward et al. | 128/662.06 |
| 5,368,035 | 11/1994 | Hamm et al. | 128/662.06 |

FOREIGN PATENT DOCUMENTS

| | | | |
|---|---|---|---|
| WO92/03095 | 3/1992 | WIPO | A61B 8/12 |

OTHER PUBLICATIONS

"Early and Present Examples of Intraluminal Ultrasonic Echography"; Bom et al., *SPIE,* vol. 1068, 1989.

Crowley et al., "Optimized Ultrasound Imaging Catheters for Use in the Vascular System"; 145–151 *International Journal of Cardiac Imaging 4;* 1989.

Crowley et al., "Ultrasound Guided Therapeutic Catheters: Recent Developments and Clinical Results"; *International Journal of Cardiac Imaging 4;* 145–156; 1991.

Ellis et al., "Tltrasonic Imaging Catheter"; *SPIE;* Jan. 12, 1988.

Gichard et al.; "Development of a Mechanically Scanned Doppler Blood Flow Catheter"; *IEEE;* 1975.

*Primary Examiner*—Francis Jaworski

[57] ABSTRACT

An ultrasound imaging device and method employing it featuring a stationary, elongated flexible tubular body, a rotatable drive shaft extending through the body, and a nose member located distally of the tubular body, the nose member mounted on the distal end of the drive shaft to rotate therewith, the nose member being of rounded atraumatic form, sized at its proximal end to substantially match the diameter of the body and an acoustic imaging transducer incorporated in the nose member for producing acoustic images of adjacent tissue as the drive shaft turns, there being an axial passage within the body for fluid flow from a proximal entry port to at least one fluid delivery port located distally of the entry port.

25 Claims, 3 Drawing Sheets

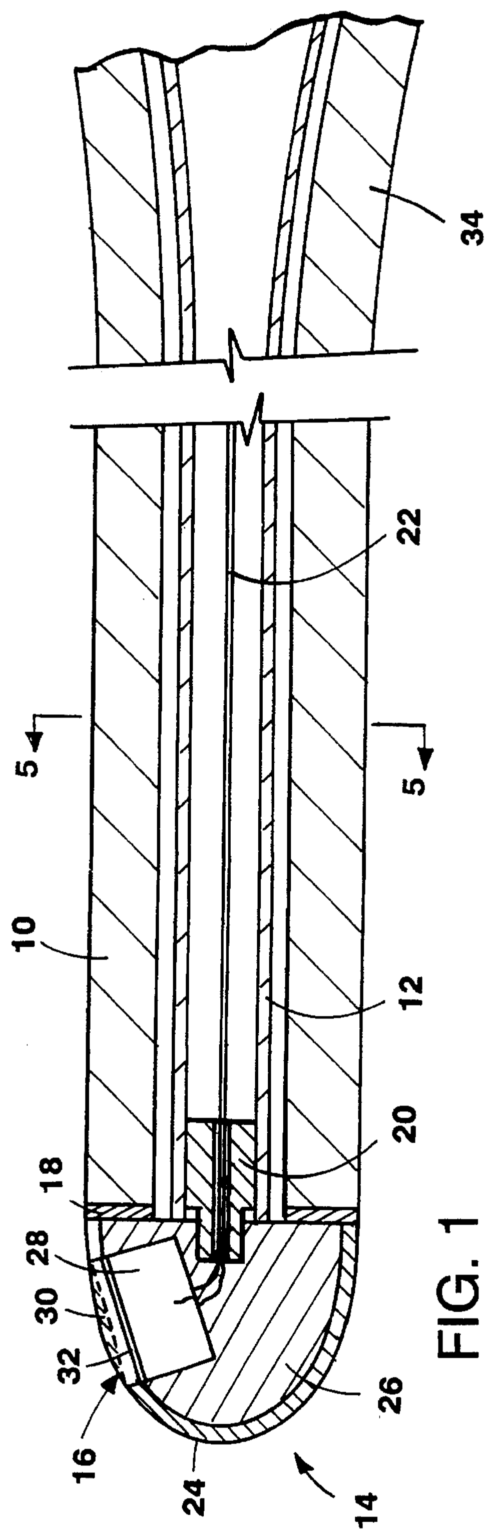
FIG. 1
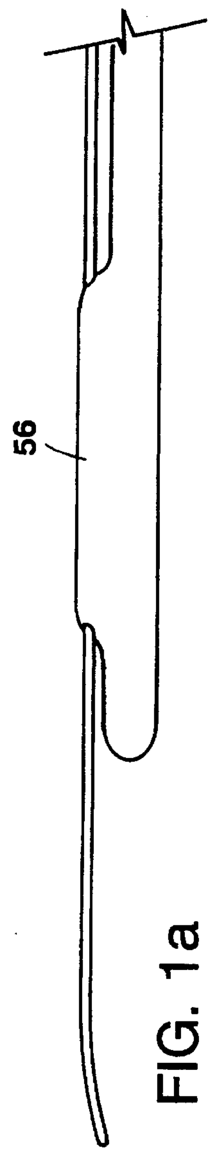
FIG. 1a
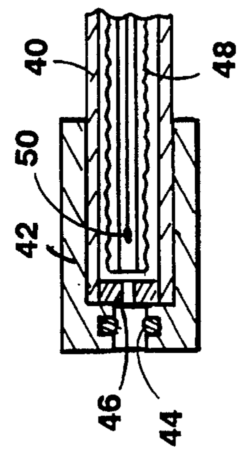
FIG. 3
FIG. 2

MEDICAL ACOUSTIC IMAGING CATHETER AND GUIDEWIRE

CROSS-REFERENCE OF RELATED APPLICATION

This is a continuation of application Ser. No. 08/067,348, filed May 25, 1993, now abandoned, which is a continuation-in-part of U.S. patent application Ser. No. 08/066,990, filed May 24, 1993 by Peter M. Nicholas et al.

BACKGROUND OF THE INVENTION

This invention relates to low profile guidewire-like and catheter-like devices for ultrasonic imaging of regions within the body.

Some of the features needed for a commercially practical design of such imaging devices are a construction that enables it to be conveniently made in a range of small sizes down to very small size, a distal end which can exert a degree of distal thrust to access parts of the body easily, and a tip which is non-traumatic so that it does not enter delicate linings of blood vessels or other ducts of the body.

It is also desirable for many such devices that their transducers not only be capable of high frequencies as used in existing ultrasound imaging catheters and guidewires but also for much higher frequencies, e.g. for closer imaging.

Ultrasonic imaging devices should also have usual guidewire-like qualities or catheter-like qualities, for instance variable stiffness along their length. A more flexible distal portion enables access to difficult-to-access regions of the body, while a stiffer proximal region of the catheter or guidewire enables pushing and manipulation. For instance, when imaging the coronary arteries, it is desirable to readily place a device in the femoral artery through a coronary guiding catheter, around the aortic arch and into the coronary ostium. Generally the guiding catheter only extends up to but not into the coronary ostium. With an appropriate design of an ultrasound device, with a very flexible distal portion, it becomes possible to exert good control over the imaging tip that is placed directly from the coronary ostium into the more distal region of the coronary artery.

It is also desirable to provide an acoustic imaging device which is immediately usable rather than having to prepare a device specially by injection of water or saline or other fluid acoustic coupling medium.

It has been known to employ an acoustic imaging catheter which has the additional capability of fluid and drug delivery. It is desirable to achieve ways of doing this with improved or different versions of catheters that are produced to better fulfill the needs of physicians.

With prior designs, it has not been feasible to achieve all desirable combinations of the above features.

SUMMARY OF THE INVENTION

According to one important aspect of the invention, an ultrasound imaging device is provided comprising a stationary, elongated flexible tubular body, a rotatable drive shaft extending through the body, and a nose member located distally of the tubular body, the nose member mounted on the distal end of the drive shaft to rotate therewith, the nose member being of rounded atraumatic form, sized at its proximal end to substantially match the diameter of the body and an acoustic imaging transducer is incorporated in the nose member for producing acoustic images of adjacent tissue as the drive shaft turns.

Various preferred embodiments have one or more of the following features.

A bearing is disposed between the nose member and the distal end of the catheter, tension being maintained on the drive shaft to maintain the nose member engaged with the distal end of the body via the bearing.

A thrust bearing is joined to a proximal portion of the drive shaft and transmits thrust from the shaft to the proximal end of the body to maintain the tension in the shaft.

The body is formed at least in its distal region of non-sonolucent body material. Preferably in the form of a catheter, the body is formed of non-sonolucent polymer. Preferably, in the form of a guidewire, the body of the catheter is formed of metal.

The transducer lies substantially at the surface of the nose member for substantially direct exposure to tissue to be imaged.

The ultrasound imaging device is combined with an ultrasound energy source adapted to drive the transducer at frequency in the range of 30 MHz to 300 MHz.

The drive shaft is comprised of a solid shaft, and a capacitive link is provided, the device constructed to transmit signals to and from the transducer via the solid shaft.

According to another aspect of the invention a method of imaging comprises providing an ultrasound imaging device according to one or more of the foregoing features, inserting a distal nose of the device and a major part of the length of the body into a patient, rotating the transducer at imaging speed while energizing the transducer at imaging frequency and producing an image from the return signal for viewing.

According to another important aspect of the invention a device is provided with features as described above and there is provided an axial passage within the body of the device for fluid flow from a proximal entry port to at least one fluid delivery port located distally of the entry port.

Various preferred embodiments of this aspect have one or more of the following features.

An end bearing is disposed between the nose member and the distal end of the catheter, tension being maintained on the drive shaft to maintain the nose member engaged with the distal end of the body via the bearing to maintain a seal against unwanted fluid leakage from an adjacent portion of the axial passage. Preferably a thrust bearing is joined to a proximal portion of the drive shaft and transmits thrust from the shaft to the proximal end of the body to maintain tension in the shaft, and pressure between the nose member and the end bearing.

An end bearing is disposed between the nose member and the distal end of the catheter, there being at least one fluid delivery passage extending through the end bearing from the axial passage to the delivery port. Preferably the bearing comprises a hub portion and an end flange portion, there being at least one axial passage along the hub portion and at least one intersecting radial passage in the end flange portion terminating at the delivery port.

The body of the device is formed at least in its distal region of body material through which delivery holes extend.

The transducer lies substantially at the surface of the nose member for substantially direct exposure to tissue to be imaged, and the delivery port is located closely adjacent to the transducer in position to deliver fluid in the region of tissue being imaged.

The device is combined with an ultrasound energy source adapted to drive the transducer at frequency in the range of 30 MHz to 300 MHz.

Another aspect of the invention is a method of imaging comprising providing an ultrasound imaging device according to the features described above, inserting a distal nose of the device and a major part of the length of the body into a patient, rotating the transducer at imaging speed while energizing the transducer at imaging frequency and producing an image from the return signal for viewing, and employing a fluid passage and delivery port in the device to deliver fluid to regions accessed by the device.

In preferred embodiments of this aspect of the invention, the delivery port is located adjacent the transducer, and the port is used to deliver drug to the region of tissue being imaged.

BRIEF DESCRIPTION OF THE DRAWING

FIG. 1 shows a longitudinal cross-sectional view of the catheter or guidewire imaging device.

FIG. **1*a* is a side view of a catheter having a construction similar to that of FIG. 1**, and having in addition, a saddle for introduction of the catheter over a guidewire.

FIG. 2 is a longitudinal cross-sectional view on an enlarged scale of the proximal end of the catheter or guidewire imaging device of FIG. 1 showing a male electrical connector.

FIG. 3 is a longitudinal cross-sectional view of the same scale as FIG. 2 of a mating female connector which accepts the connector of FIG. 2.

Figure 4:
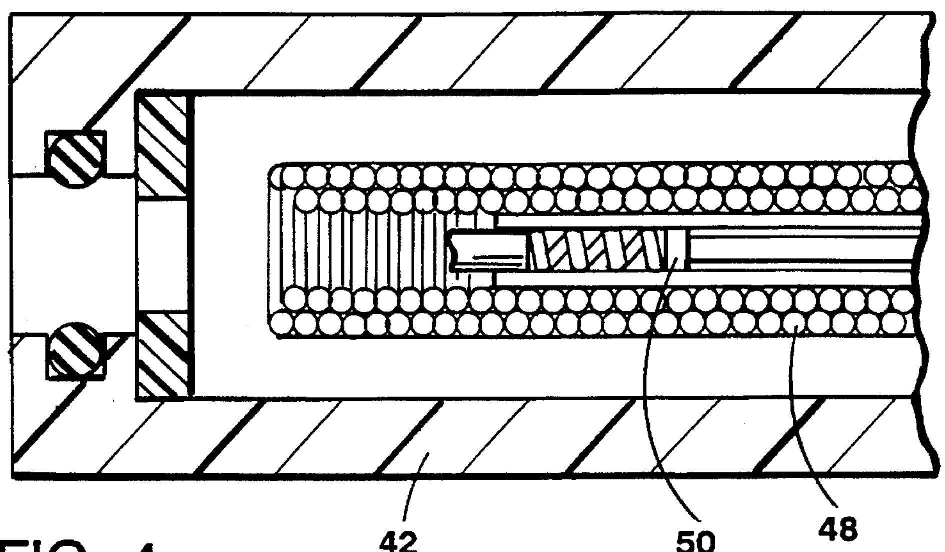

FIG. 4 is a longitudinal cross-sectional view on a considerably enlarged scale that shows the detail of a multifilar drive shaft and sliding pin arrangement for making electrical and mechanical contact simultaneously.

Figure 5:
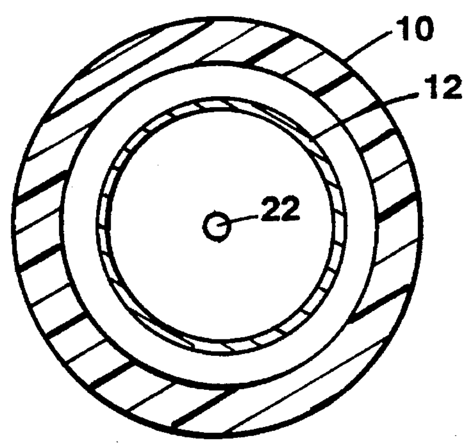

FIG. 5 is a transverse cross-sectional view of the distal portion of the device of FIG. 1 taken on line 55 of FIG. 1.

Figure 6:
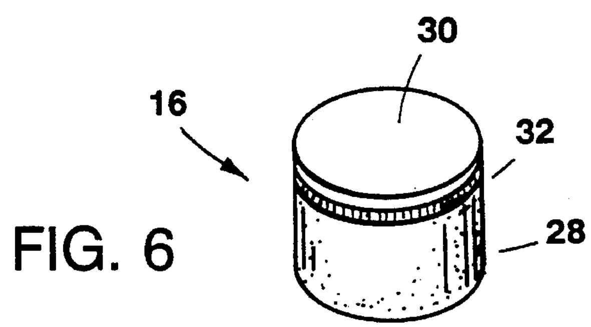

FIG. 6 is a perspective view of a transducer assembly formed from a slab to material.

Figure 7:
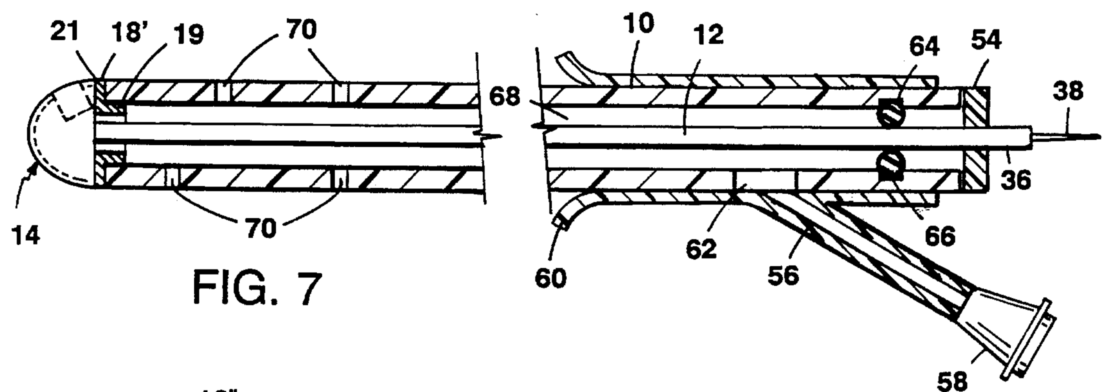

FIG. 7 is a longitudinal cross-sectional view of another preferred embodiment which enables combined imaging and fluid infusion or drug delivery.

Figure 8:
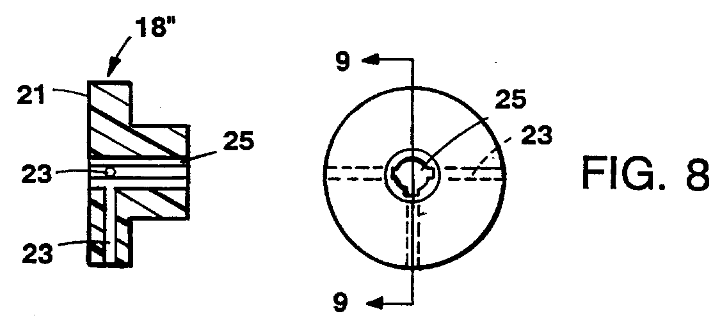

FIG. 8 is an end view of a distal end bearing which enables fluid infusion or drug delivery near the distal tip.

Figure 9:
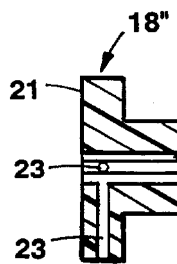

FIG. 9 is a cross-sectional view of the end bearing taken on line 9—9 of FIG. 8.

DESCRIPTION OF THE PREFERRED EMBODIMENTS

A preferred device has an elongated body 10 which houses rotary shaft 12 to which is attached transducer assembly 14 in which is mounted transducer 16. As a means for firmly attaching shaft 12 to the transducer assembly 14, a boss 20 is employed comprising a metallic plug which is press-fit into rotary shaft 12. Passing through boss 20 is wire 22 which extends from the conductive backing 28 of the transducer 16 and passes through shaft 12 to the proximal portion of the device. Transducer assembly 14 includes metal-epoxy filler 26 which forms a coherent, generally semi-spherical nose member which is coated with smooth epoxy coating 24. Transducer 16 comprises conductive backing 28, piezoelectric (PZT) layer 32 and conductive lens 30. For attaching transducer assembly 14 securely to shaft 12, boss 20 comprises a stepped hollow stainless steel bushing which is press-fit both into shaft 12 with an interference press fit and into the metal epoxy-filled transducer assembly.

As an alternative, the boss may be glued or otherwise bonded to the epoxy-filled assembly.

The transducer assembly 14 as shown has a generally hemispherical form. It may in other embodiments be blunt, a perfect hemisphere, or of slightly bullet-shaped elongated form, but in any case it provides a smooth, symmetric, atraumatic shape for exposure to body tissue and has a base diameter that substantially corresponds to the diameter of body 10. These parts are positioned close together to provide a uniform, atraumatic transition from moving end to stationary body without exposed sharp edges.

In use, transducer assembly 14 receives a degree of distal force as it passes into regions of the body and it receives lateral forces. To enable free rotation and yet prevent the transducer assembly 14 from changing its position relative to elongated body 10, end bearing 18 is provided. Bearing 18 is of flat annular form, made of teflon or stainless steel coated teflon, and is inserted between the proximal end of transducer assembly 14 and the distal end of body 10 to provide a low friction bearing surface that prevents galling of the surfaces and also limits lateral movement while still allowing rotation of transducer assembly 14 and shaft 12.

Referring to FIG. 2, shaft 12 extends through elongated body 10 to beyond its proximal end. It is held in place by proximal thrust bearing 54 which is firmly attached to ring 36. Ring 36 also holds tip 38 and forms an electrical connector. The position of ring 36 creates a slight tension on shaft 12 (or, in other embodiments, compression in elongated body 10, or both) to maintain the position of transducer assembly 14 firmly on the ends of body 10.

Transducer 16 is a solid layered structure cut from a pre-formed slab. In forming a slab, conductive backing material 28 is first formed by mixing particles of tungsten or gold with an epoxy filler. Onto this backing is placed a layer 32 of ceramic material which is piezoelectric such as lead zirconate titinate, otherwise referred to as PZT. On top of the PZT layer 32 is formed another conductive layer of metal epoxy such as silver conductive epoxy, which forms a conductive lens 30. The pre-formed slab may be cut to form a small cube, rectangle or, in the case of the presently preferred embodiment, cylinder.

The angle of the transducer 16 and transducer assembly 14 is tilted slightly forward to reduce specular reflection from nearby surfaces. The angle may be between five degrees and ten degrees for the purpose of reducing specular reflections. For a more forward look and to create a conical scan as might be desirable in imaging more distal regions of the anatomy, transducer 16 may be angled at a larger angle including nearly pointing forward, i.e. up to about 80 degrees forward.

Transducer 16 is shown in perspective view in detail in FIG. 6. It comprises a cylindrical plug of sandwiched material pre-formed prior to insertion. Lens 30 is the uppermost layer and may be either flat or concave for focusing. PZT layer 32 is generally flat, sandwiched between the two layers 28 and 30 while backing layer 28 comprises the bulk of the assembly, serving to absorb the acoustic backwave from PZT layer 32, allowing a short pulse to be produced, which is effective for close up imaging.

Transducer 16 is placed on one side of assembly 14.

To provide a smooth exterior surface, epoxy coat 24 is applied either by spraying or dipping, and then finally finished by grinding or polishing to provide an atraumatic smooth outer surface that can conduct ultrasound.

With such construction, the device is capable of imaging at frequencies that are similar to current intravascular ultrasound imaging practice, e.g., in the region from 8 to 30 MHz. The construction principles are also effective in the region of 30 to 300 MHz by virtue of the direct view of the surrounding tissue (i.e. without the need of the ultrasound to pass through a catheter wall or relatively thick window). Only a very thin epoxy coating layer, e.g. a thickness of one or a few thousandths of an inch or less may be employed for achieving the atraumatic surface over the transducer.

FIG. 3 shows a connector assembly for simultaneously making electrical and mechanical connection with the imaging guidewire or catheter assembly, linking the device to an ultrasound imaging console that has a motor driving circuit and electrical wires of commutation circuit. In FIG. 3, the proximal driver casing 40 is capped with proximal driver bushing 42. A tight fitting O-ring 44 is placed in the gland in proximal driver bushing 42. This creates an interfering state for body 10 when it is inserted into proximal driver bushing 42. In order to prevent the guidewire or catheter from being inserted too far, stop 46 is fixed inside of proximal driver bushing 42. To receive electrical connector, ring 36 and tip 38, a multifilar dual post drive shaft 48 (see FIG. 4) is modified with an open end so that it may accept the stub of tip 38 and ring 36 of the device in interfering fashion while making simultaneous electrical and rotary mechanical connection. For this purpose, a spring-center contact 50 is provided with a spring behind a sliding contact within multifilar drive shaft 48. The proximal end of the device is sized to fit into the drive shaft with interference when the proximal end of the device is inserted into proximal driver bushing 42. O-ring 44 engages body 10 and holds the device securely in place while preventing bushing 54 from extending past stop 46.

When constructed for use as a catheter, the device is no larger than about 10 French and about 150 centimeters long. Such a device is useful for imaging portions of the heart. With such a construction a large transducer is employed capable of relatively deep penetration of heart tissue, using ultrasound frequencies in the range of about 8 MHz.

A smaller size catheter, of about 6 French and 150 centimeters length, is useful for imaging in the peripheral vessels, the chambers of the heart, the great arteries and veins, and also in other non-vascular ducts and ports of the body.

A smaller catheter size in the range of 4 French and about 150–175 centimeters length is useful for imaging the regions previously mentioned, and in addition, smaller arteries including possibly coronary arteries and arteries such as the carotid artery extending from the aortic arch, as well as in non-vascular regions.

A smaller size of about 3 French and 150–175 centimeters length is also useful for imaging mid-coronary arteries, distal coronary arteries and more distal regions of the carotid artery including the brain and the regions beyond the brain. A catheter of this size is also useful for imaging the tubular arteries and the distal extremities.

With all of these catheters just described, because there is no need for a relatively thick acoustic window to pass the ultrasound signal, acoustic loss is reduced that can limit penetration and resolution. Since window thickness produces attenuation and refraction which increases in proportion to frequency of operation, it follows that with the device of the present invention higher frequencies than 30 MHz may be successfully employed.

In fact, frequencies as high as 300 MHz are contemplated for very close-up imaging of the interior of blood vessels and arteries, veins, ducts and other areas of surrounding tissue where the device can be placed.

The device of the invention is contemplated to be particularly useful as a pre-assessment and post-assessment device with angioplasty. In angioplasty a balloon or a lesion-reducing means is inserted into the patient's artery and either a mechanical action or a rotary cutting action is used to change and open up or recanalyze the patient's artery. The present imaging device is used for passing into that region both before and after a procedure is conducted. The device is used to observe the nature of the stenosis, its extent, its diameter, its texture and also whether or not there are residual flaps, cracks, or other conditions which may cause problems later such as reocclusion or emboli.

Another embodiment of the device is shown in FIG. 1*a*. A catheter of the construction of FIG. 1 is provided with a "side saddle" 56. This feature is mounted along side and parallel to body 10 and is constructed to receive and ride upon a guidewire. It has a distal orifice positioned proximal to transducer assembly 14, and it continues along catheter body 10 for a distance of between a half centimeter and 75 centimeters, depending on the application, and has a proximal opening which allows the guidewire to exit.

This feature is useful for positioning the device within the peripheral vasculature, the iliac, the femoral, the aorta, the aortic arch, the heart, the distal extremities, the carotid artery and other blood vessels where a catheter with a side guidewire may be passed, or any other region of the body which has a duct, an orifice, or a tube in which a guidewire may first be placed and a catheter of this kind slid along the guidewire. There is also the possibility of using this guidewire-sided device in the coronary arteries.

Below 3 French in size, the device has guidewire-like properties. Guidewires tend to begin in the diameter range of 0.038 inches, extending down to as small as 0.10 inches.

An 0.035 inch diameter device constructed according to FIG. 1 can serve as an ultrasound imaging guidewire-type device, as there are many interventional accessories which have lumens which, for being guided into position, will slide over an 0.035 inch wire. A device of that size is contemplated to be useful by itself for imaging the coronary arteries (i.e. not serving as a guidewire). It also is contemplated as useful to serve as a guidewire for passing dilatation balloons used in the peripheral artery such as the ileac, the femorals and the aorta, or the umbiliary tree or in areas of the esophagus or the anus.

A device of 0.035 inch diameter may also be used to recanalyze or unblock arteries which are totally occluded that are sized approximately with an 0.035 inch guidewire. For an example, the femoral artery which is long may become totally occluded over a length of 2, 3 or even 20 centimeters. Frequently, this condition is treated by the application of a clot-dissolving enzyme such as urokinase, TpA or pro-urokinase over a period of time. This creates patient discomfort, is very expensive and time consuming, and one cannot tell when the job is done. An alternative to such treatment has been rotational recanalization using a slow rotation and thrusting motion of a rotating guidewire. Also lysing guidewires have been used, as reported in the medical literature.

We contemplate the present device can be used as a rotating drive shaft that is exposed to the blood or placed inside of a sheath, which slowly rotates and massages its way through the blocked artery either by separating or lysing (through a suitable drug delivery passage, not shown) or otherwise moving the blood clot or tissue out of the way to recanalyze the blood vessel. The acoustic imaging device of the invention can thus be used to create a distal thrusting force and a slow rotational force to create an outward force that separates the tissue and finds its way through the lumen.

It is recognized that imaging of tissue in direct contact with the transducer 16 is not desirable because solid reflecting tissue and contact with acoustic imaging transducers harms image quality and creates image clutter which makes it difficult to visualize the scene.

However, we contemplate to use the device in the following manner. First it is used to thrust forward and recanalyze the artery. Then it is backed off to allow blood to fill the space that is created. Then the device is used to image the region of the body that has been treated using the refilled blood as the coupling medium.

The next size down from 0.035 inch which is commonly used is a 0.031 inch guidewire. These are generally 180 centimeters long. An 0.025 inch can also be 165 centimeters long. Its use is substantially the same as described above for the 0.035 inch device except it can reach somewhat more distal arteries and ducts and somewhat smaller diameters. Balloon devices may be introduced over it.

The device of the next typical guidewire size, 0.018 inch, retains its guidewire-like quality and may be passed through an introducer through a coronary guiding catheter, up to the coronary ostium, beyond the coronary ostium into the proximal mid and distal coronary arteries and used to successfully image those portions of the artery. A balloon dilatation catheter may then be passed over the proximal end of the pre-placed device and introduced into the coronary arteries. Imaging with the device can be used to guide the location and the use of the balloon dilatation catheter in the coronary artery.

The next smaller size of this device is 0.014 inch in diameter. At present, this is the smallest size guiding type of guidewire that is commonly used in the coronary arteries. Because of its shaft construction and body construction, the device of the present invention, in this size, is contemplated to give good lateral support and minimum traumatic tip profile. Even smaller sizes are contemplated as feasible.

At these particularly small diameters, transducer 16 is very small, even less than 0.008 inch in diameter in certain instances. One might think this would present particular problems because it is known that the beam shape of a transducer is defined as $D^2/4\lambda$ where D is the maximum diameter of the transducer emitting surface and $\lambda$ is the acoustic wavelength being employed. At very small diameters, using present common ultrasound frequencies, the ultrasonic transducer does not produce a beam as needed for imaging but rather produces a pattern similar to that produced by a point source which is not generally useful in imaging.

However, because of the direct exposure of the transducer according to the present invention (no intervening, relatively thick wall or window), much higher ultrasound frequencies may be employed. The device is connected to a source of frequencies between 30 MHz and 300 MHz. Use of such frequencies, made possible in a practical way by the construction according to the invention, achieves an optimal relationship between the diameter of the device and the wavelength and thus provides a coherent beam useful to obtain images.

Various kinds of drive shafts 12 may be employed in preferred embodiments. In one embodiment, the drive shaft is made in tubular form of the elastic alloy known as nitinol. The nitinol alloy may be tapered or (i.e., flared) to provide graduated stiffness over the length of the overall device, shaft 12 providing some lateral support to body 10. In another embodiment, a solid nitinol shaft is used.

In an alternative embodiment, a dual multifilar drive shaft similar to that described in U.S. Pat. No. 4,951,677 may be employed.

Flare or taper 34 to the shaft as shown in FIG. 1 achieves advantages. In certain cases rotational fidelity of shaft 12 is more fully achieved if the drive shaft starts out with a proximal diameter which is larger than the distal diameter.

Another advantage of having such taper or flare 34 is that the lateral stiffness of body 10 can thus be varied as a function of its position and length. For instance, the body in the proximal portion for its first 40 centimeters or so may be of one diameter, say 0.035 inches, whereas body 10 may taper down in a short transition region and in its distal region, over the remainder of the 115 to 125 centimeters length it may be 0.025 inches or less in diameter.

Use of multiple diameters over the length of the device, either stepped or gradually tapered, with both catheter and guidewire constructions may be used to provide desired degrees of lateral stiffness and trackability essential to achieving access to selected regions of the body.

Depending upon the application and the diameter of the device to be made, several different materials may be selected for fabrication of the elongated body 10. In catheter configurations, body 10 is for instance made of a material such as teflon, nylon or urethane or other catheter body materials. It may have embedded a metal shield of either wound or braided construction or it may have a metallized layer to provide electrical shielding. It is an advantage of the present invention that the material of the distal region integral with the remaining portions of the body can be selected only for its desirable catheter properties without need to require it be sonolucent.

In guidewire sizes, to achieve greater desired lateral stiffness of body 10, non-polymeric materials may be employed such as nitinol tubing which can be coated with a suitable antithrombogenic coating or with an outer layer of teflon to make the outside surface smooth. In other embodiments, the body may consist of metal coils of wire which are overwrapped with layers of mylar or layers of shrunk teflon tube or polyethylene tube, again with the advantage that there need be no concern for the sonolucency of the body.

This feature is particularly important in metallic versions where body 10 is made out of e.g. nitinol or stainless steel tube or rod or some other wrapped, wound construction since it is often very difficult to provide acoustic windows through such types of materials.

In another preferred embodiment, shaft 12 is made of a solid single conductive rod which may be tapered, e.g. of nitinol wire for superior rotational fidelity without taking a set. Such a construction presents the problem of how to obtain the return signal to the imaging console since only one conductive member may be used. According to the present invention, this difficulty is overcome by first gold-plating shaft 12 and then overcoating it with a di-electric coating. Then over a portion of its length, for instance 5 to 10 centimeters from the distal end, the di-electric coating is again overcoated with another gold layer which is insulated from the first gold layer.

The transducer semi-conductor is connected to the first gold layer and signal from it is carried back to the imaging console on the metallic shaft. The transducer return path through the gold or conductive lens 30 is brought back to the outer gold layer where it makes no DC connections to anything except to the cylindrical portion described by the second gold layer. This is capacitively coupled to a metallic layer embedded in body 10 which extends back to signal wires through catheter body 10, thence to the imaging console, to complete a suitable acoustic electrical return path.

A further embodiment enables acoustic imaging with devices of the type described combined with features enabling infusing a drug or a clot-dissolving enzyme. This is useful to deliver drug or clot-dissolving enzyme in a region of the body which may be blocked or stenosed or have a lesion that supports thrombus which may be hardened.

Referring to FIG. 7, body 10 is provided with a proximal entry side hole 62 which is exposed for alignment with detachable fluid introduction sidearm adaptor 56. Detachable sidearm adaptor 56 is equipped with leuer fitting 58, entry flare 60 and a barrel body surrounding body 10.

Entry flare 60 enables the detachable sidearm adaptor 56 to be conveniently slid in position over body 10 while the main barrel portion of the adaptor provides a tight, interfering seal with the exterior surface of body 10 to prevent fluid from escaping from either side of entry port 62. To prevent fluid from migrating proximally inside the body 10, O-ring 64 is disposed in O-ring gland 66 around rotating shaft 12. Leuer fitting 58 at the end of detachable sidearm adaptor 56 is adapted to receive an injection syringe to inject fluid under pressure. The fluid enters through proximal side port 62 into the axial passage 68 of the device, between the drive shaft 12 and the internal bore of body 10.

Referring still to FIG. 7, the distal portion of body 10 is provided with infusion holes 70 that communicate with axial passage 68 to enable transfer of fluid from the proximal side hole 62 to the desired region in the patient. Fluid is prevented from substantial leakage at the distal end by thrust bearing 18' disposed between transducer nose assembly 14 and the distal end of body 10. Body 10 is provided with an infusion hole 70 in a selected location or a set of such holes arranged in selected positions and in predetermined number and size to accommodate the desired treatment. These parameters vary with such variables as type of catheter tip, catheter style, size and shape, and type of treatment to be administered.

For instance, discrete focal lesions may be treated by infusion holes which are placed in concentration near the distal end of the catheter. Long distributed lesions may be best treated by placing the infusion holes in a broad and even distribution over a long portion of the body 10.

In the embodiment of FIG. 7, end bearing 18' is comprised of hub portion 19 and flange portion 21. The flange portion of bearing 18' forms a rotating slidable end surface for transducer assembly 14 to bear against endwise when the distal end of the device is pushed against an obstruction. Hub 19 provides a cylindrical bearing surface which resists lateral movement of the shaft and transducer assembly relative to body 10. Together the hub and flange are effective to form a fluid seal and to stabilize the transducer assembly 14, enabling it to withstand lateral and axial forces while still retaining the ability of the assembly to rotate as driven by drive shaft 12.

As an alternative to the infusion system based on holes 70 in the body 10, as shown in FIG. 7, FIGS. 8 and 9 show end bearing 18" equipped with radial passages 23 connected to axial passages 25 and outlet port. This construction is effective to enable fluid to pass through end bearing 18" and reach tissue immediately within the field of view of the transducer. The axial passage 25 can be provided by machining a standard woodruff keyway in a bearing member, or the member may be of molded construction formed in other ways. In FIG. 8, three such keyways are shown, one at the bottom and two at the sides. These intersect with drilled radial passages 23 shown in the side view in FIG. 9, at the bottom, and in the end view of FIG. 9 in the center.

What is claimed is:

1. An ultrasound imaging device comprising a stationary, elongated flexible tubular body, a rotatable drive shaft extending through said body, and a nose member at least a portion of which is located entirely distally of said entire stationary tubular body, said nose member being mounted on the distal end of said drive shaft to rotate therewith relative to said stationary tubular body, said nose member being of rounded atraumatic form, being sized at its proximal end to substantially match the diameter of said body, and having an acoustic imaging instrument incorporated in said nose member for producing acoustic images of adjacent tissue as said drive shaft turns, said acoustic imaging instrument being located entirely distally of said entire stationary tubular body, there being an axial passage within said body for fluid flow from a proximal entry port to at least one fluid delivery port located distally of said entry port.

2. The ultrasound imaging device of claim 1 in which an end bearing is disposed between said nose member and the distal end of the stationary tubular body, tension being maintained on said drive shaft to maintain said nose member engaged with the distal end of said body via said bearing to maintain a seal against unwanted fluid leakage from an adjacent portion of said axial passage.

3. The ultrasound imaging device of claim 2 including a thrust bearing joined to a proximal portion of said drive shaft and transmitting thrust from said shaft to the proximal end of the body to maintain tension in said shaft, and pressure between said nose member and said end bearing.

4. The ultrasound imaging device of claim 1 in which an end bearing is disposed between said nose member and the distal end of the stationary tubular body, there being at least one fluid delivery passage extending through said end bearing from said axial passage to said delivery port.

5. The ultrasound imaging device of claim 1 wherein said body is formed at least in its distal region of body material through which fluid delivery ports extend.

6. The ultrasound imaging device of claim 1 in which said acoustic imaging instrument lies substantially at the surface of said nose member.

7. The ultrasound imaging device of claim 6 in combination with an ultrasound energy source adapted to drive said acoustic imaging instrument at frequency in the range of 30 MHz to 300 MHz.

8. The ultrasound imaging device of claim 6, wherein said delivery port is located closely adjacent to said acoustic imaging instrument in position to deliver fluid in the region of tissue being imaged.

9. The ultrasound imaging device of claim 1 wherein said acoustic imaging instrument comprises a transducer.

10. An ultrasound imaging device comprising a stationary, elongated flexible tubular body, a rotatable drive shaft extending through said body, and a nose member located distally of said tubular body, said nose member mounted on the distal end of said drive shaft to rotate therewith, said nose member being of rounded atraumatic form, sized at its proximal end to substantially match the diameter of said body and an acoustic imaging transducer incorporated in said nose member for producing acoustic images of adjacent tissue as said drive shaft turns, there being an axial passage within said body for fluid flow from a proximal entry port to at least one fluid delivery port located distally of said entry port, wherein an end bearing is disposed between said nose member and the distal end of the stationary tubular body, there being at least one fluid delivery passage extending through said end bearing from said axial passage to said delivery port, and wherein said bearing comprises a hub portion and an end flange portion, there being at least one axial passage along said hub portion and at least one intersecting radial passage in said end flange portion terminating at said delivery port.

11. A method of imaging comprising providing an ultrasound imaging device comprising a stationary, elongated flexible tubular body, a rotatable drive shaft extending through said body, and a nose member at least a portion of which is located entirely distally of said entire stationary tubular body, said nose member being mounted on the distal end of said drive shaft to rotate therewith relative to said stationary tubular body, said nose member being of rounded atraumatic form, being sized at its proximal end to substantially match the diameter of said body, and having an acoustic imaging instrument incorporated in said nose member for producing acoustic images of adjacent tissue as said drive shaft turns, said acoustic imaging instrument being located entirely distally of said entire stationary tubular body, there being an axial passage within said body for fluid flow from a proximal entry port to at least one fluid delivery port located distally of said entry port, inserting a distal nose of the device and a major part of the length of the body into a patient, rotating the acoustic imaging instrument at imaging speed while energizing said acoustic imaging instrument at imaging frequency, producing an image from the return signal for viewing, and employing said fluid passage and delivery port to deliver fluid to regions accessed by said device.

12. The method of claim 11 in which said delivery port is located adjacent said acoustic imaging instrument, and using said port to deliver a drug to the region of tissue being imaged.

13. An ultrasound imaging device comprising a stationary, elongated flexible tubular body, a rotatable drive shaft extending through said body, and a nose member at least a portion of which is located entirely distally of said entire stationary tubular body, said nose member being mounted on the distal end of said drive shaft to rotate therewith relative to said stationary tubular body, said nose member being of rounded atraumatic form, being sized at its proximal end to substantially match the diameter of said body, and having an acoustic imaging instrument incorporated in said nose member for producing acoustic images of adjacent tissue as said drive shaft turns, said acoustic imaging instrument being located entirely distally of said entire stationary tubular body, said acoustic imaging instrument lying substantially at the surface of said nose member.

14. The ultrasound imaging device of claim 13 in which a bearing is disposed between said nose member and the distal end of the stationary tubular body, tension being maintained on said drive shaft to maintain said nose member engaged with the distal end of said body via said bearing.

15. The ultrasound imaging device of claim 14 including a thrust bearing joined to a proximal portion of said drive shaft and transmitting thrust from said shaft to the proximal end of the body to maintain said tension in said shaft.

16. The ultrasound imaging device of claim 13 wherein said body is formed at least in its distal region of non-sonolucent body material.

17. The ultrasound imaging device of claim 16 in the form of a catheter, the body of said catheter being formed of non-sonolucent polymer.

18. The ultrasound imaging device of claim 16 in the form of a guidewire, the body of said guidewire being formed of metal.

19. The ultrasound imaging device of claim 13 in combination with an ultrasound energy source adapted to drive said acoustic imaging instrument at frequency in the range of 30 MHz to 300 MHz.

20. The ultrasound imaging device of claim 13 in which said drive shaft is comprised of a solid shaft, and a capacitive link is provided, the device being constructed to transmit signals to and from the acoustic imaging instrument via the solid shaft.

21. The ultrasound imaging device of claim 20 wherein said acoustic imaging instrument comprises a transducer.

22. A method of imaging comprising providing an ultrasound imaging device comprising a stationary, elongated flexible tubular body, a rotatable drive shaft extending through said body, and a nose member at least a portion of which is located entirely distally of said entire stationary tubular body, said nose member being mounted on the distal end of said drive shaft to rotate therewith relative to said stationary tubular body, said nose member being of rounded atraumatic form, being sized at its proximal end to substantially match the diameter of said body, and having an acoustic imaging instrument incorporated in said nose member for producing acoustic images of adjacent tissue as said drive shaft turns, said acoustic imaging instrument being located entirely distally of said entire stationary tubular body, said acoustic imaging instrument lying substantially at the surface of said nose member, inserting a distal nose of the device and a major part of the length of the body into a patient, rotating the acoustic imaging instrument at imaging speed while energizing said acoustic imaging instrument at imaging frequency, and producing an image from the return signal for viewing.

23. The method of claim 22 further comprising the step of rotating said nose member while thrusting said nose member through a blood vessel to recanalyze said blood vessel.

24. An ultrasound imaging intravascular catheter comprising a stationary, elongated flexible tubular catheter body sized for use within a blood vessel, a rotatable drive shaft extending through said catheter body, and a nose member at least a portion of which is located entirely distally of said entire stationary tubular catheter body, said nose member being mounted on the distal end of said drive shaft to rotate therewith relative to said stationary tubular catheter body, said nose member being of rounded atraumatic form, being sized at its proximal end to substantially match the diameter of said catheter body, and having an acoustic imaging instrument incorporated in said nose member for producing acoustic images of adjacent tissue as said drive shaft turns, said acoustic imaging instrument being located entirely distally of said entire stationary tubular catheter body, said acoustic imaging instrument lying substantially at the surface of said nose member.

25. An ultrasound imaging intravascular guidewire comprising a stationary, elongated flexible tubular body having dimensions suitable for use of said tubular body as an intravascular guidewire, a rotatable drive shaft extending through said body, and a nose member at least a portion of which is located entirely distally of said entire stationary tubular body, said nose member being mounted on the distal end of said drive shaft to rotate therewith relative to said stationary tubular body, said nose member being of rounded atraumatic form, being sized at its proximal end to substantially match the diameter of said body, and having an acoustic imaging instrument incorporated in said nose member for producing acoustic images of adjacent tissue as said drive shaft turns, said acoustic imaging instrument being located entirely distally of said entire stationary tubular body, said acoustic imaging instrument lying substantially at the surface of said nose member.

* * * * *

UNITED STATES PATENT AND TRADEMARK OFFICE
CERTIFICATE OF CORRECTION

PATENT NO. : 5,464,016

DATED : November 7, 1995

INVENTOR(S) : Nicholas et al.

It is certified that error appears in the above-identified patent and that said Letters Patent is hereby corrected as shown below:

Title page, Col. 2, line 16,

In the References Cited section, in the "Ellis" reference "Tltrasonic" should be --Ultrasonic--.

Signed and Sealed this

Twenty-eighth Day of January, 1997

Attest:

BRUCE LEHMAN

*Attesting Officer* *Commissioner of Patents and Trademarks*